United States Patent [19]

Iwasaki et al.

[11] Patent Number: 5,066,669
[45] Date of Patent: Nov. 19, 1991

[54] BENZOFURAN DERIVATIVES

[75] Inventors: Tameo Iwasaki, Nishinomiya; Masaki Sugiura, Kawanishi; Yuzo Matsuoka, Toyonaka; Mamoru Matsumoto, Nara; Kazuyuki Kitamura, Urawa, all of Japan

[73] Assignee: Tanabe Seiyaku Co., Ltd., Osaka, Japan

[21] Appl. No.: 489,565

[22] Filed: Mar. 7, 1990

[30] Foreign Application Priority Data

Mar. 9, 1989 [JP] Japan .................................... 1-57349

[51] Int. Cl.$^5$ .................... C07D 307/77; A61K 31/34
[52] U.S. Cl. .................... 514/449; 514/450; 514/452; 514/464; 514/468; 549/299
[58] Field of Search ................ 549/299; 514/449, 450, 514/452, 464, 468

[56] References Cited

U.S. PATENT DOCUMENTS 3,704,247 11/1972 Munakata et al. ................ 549/299
4,486,445 12/1984 Patel et al. ........................ 549/299
4,897,418 1/1990 Iwasaki et al. .................... 549/299

FOREIGN PATENT DOCUMENTS 0140540 5/1985 European Pat. Off. .
0316939 5/1989 European Pat. Off. .
1509819 5/1978 United Kingdom .

OTHER PUBLICATIONS

Synthesis & Biological Screening of Some New Benzo[b]Thiophene and Naphthalene Compounds: Part III. Indian Journal of Chemistry, Sect. B, 15B(6), 555-557 [C.A. 88:74249b], H. H. Moussa et al., 1977.
Heteropolycyclic Molecules Part IX . . . H. H. Moussa et al., Journal Heterocycl. Chem. 1981, 18(8), 1519-1522, [C.A. 96:199449b].
A Synthesis of Benzothiophene Derivatives, N. R. El--Rayyes et al., Journal F. Prakt. Chem. 1975, 317(4), 552-560 [C.A. 83:206046s].
Intramolecular Diels-Alder Cyclization Into the Thiophene, L. H. Klemm et al., Journal of Heterocyclic Chemistry, 1965, 2(3), 225-227 [C.A. 63:11476c].
Synthesis of ENOL Lactones of 3-Aroyl-2-(Thienylmethylene)-Propionic Acids . . . , N. R. Guirguis et al., Liebigs Ann. Chem., 1986, (6) 1003-1011 [C.A. 105:42581g].
The Stobbe Condensation, Part V. The Cyclisation . . . , S. M. Abdel-Wahhab et al., Journal Chem. Soc. (C), 1968, (7), 867-869 [C.A. 68:114324t].

*Primary Examiner*—Catherine S. Kilby Scalzo
*Attorney, Agent, or Firm*—Browdy and Neimark

[57] ABSTRACT

A novel biphenyl derivative of the formula:

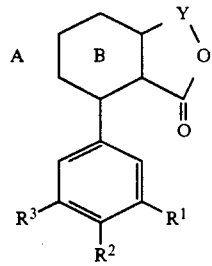

wherein Ring A is a substituted or unsubstituted sulfur-containing or oxygen-containing heteromonocyclic ring; Ring B is a ring of the formula:

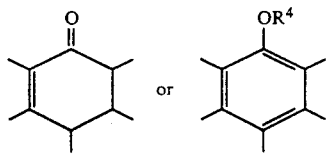

each of $R^1$ and $R^3$ is hydrogen atom, a halogen atom or a lower alkoxy group, or $R^1$ is hydrogen atom, and $R^2$ and $R_3$ are combined together to form a lower alkylenedioxy group; $R^4$ is a lower alkyl group which may have a substituent selected from a lower alkoxy group and a lower alkoxycarbonyl group; Y is methylene group or carbonyl group, and a pharmaceutically acceptable salt thereof are disclosed. Said derivative and a pharmaceutically acceptable salt thereof are useful as a therapeutic or prophylactic agent for hepatic diseases.

5 Claims, No Drawings

BENZOFURAN DERIVATIVES

This invention relates to a novel biphenyl derivative, processes for preparing the same and synthetic intermediates thereof. More particularly, it relates to a biphenyl derivative of the formula:

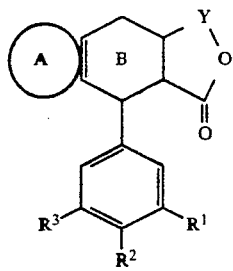
(I)

wherein Ring A is a substituted or unsubstituted sulfur-containing or oxygen-containing heteromonocyclic ring; Ring B is a ring of the formula:

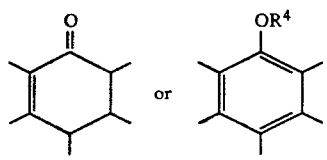

each of $R^1$ to $R^3$ is hydrogen atom, a halogen atom or a lower alkoxy group, or $R^1$ is hydrogen atom, and $R^2$ and $R^3$ are combined together to form a lower alkylenedioxy group; $R^4$ is a lower alkyl group which may have a substituent selected from a lower alkoxy group and a lower alkoxycarbonyl group; Y is methylene group or carbonyl group, or a pharmaceutically acceptable salt thereof.

The liver is an important organ having various functions such as detoxication, various metabolism, storage of nutrients or the like and is acutely or chronically injured by various causes such as virus, drugs, alcohols and so forth. These injuries bring about various hepatic diseases such as acute or chronic hepatitis, fatty liver and finally result in hepatocirrhosis. In particular, acute and chronic hepatitis and hepatocirrhosis are characterized by round cell infiltration and mesenchymal reactions such as fibrosis in the liver and the like.

It is hitherto known that Malotilate (Chemical name: diisopropyl 1,3-dithiol-2-ylidenemalonate) increases protein synthesis in the liver and is useful for the therapy of these hepatic diseases [Japanese Patent Publication (unexamined) No. 144734 (1976)]. However, this compound is known to frequently bring about hepatic hypertrophy.

The novel biphenyl derivatives (I) of the present invention and pharmaceutically acceptable salts thereof are useful to alleviate or cure hepatic injuries and also protect the liver from hepatic injuries without hepatic hypertrophy.

Examples of the compound of the present invention include those of the formula (I) in which Ring A is a 5-membered sulfur-containing or oxygen-containing heteromonocyclic ring such as thiophene or furan ring which may have a substituent selected from formyl group, a lower alkoxy-methyl group and hydroxymethyl group. Among them, pharmaceutically preferred examples include those of the formula (I) in which each of $R^1$ to $R^3$ is hydrogen atom, a halogen atom or a lower alkoxy group. More preferred examples include those of the formula (I) in which Ring A is thiophene or furan ring which may be substituted with hydroxymethyl group, $R^1$ is hydrogen atom or a lower alkoxy group, each of $R^2$ and $R^3$ is a lower alkoxy group, and $R^4$ is a lower alkyl group. Most preferred examples are those of the formula (I) in which Ring A is thiophene ring, Ring B is a ring of the formula:

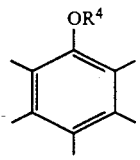

$R^1$ is hydrogen atom, each of $R^2$ and $R^3$ is methoxy group, and $R^4$ is methyl group, and those of the formula (I) in which Ring A is furan ring which may be substituted with hydroxymethyl group, Ring B is a ring of the formula:

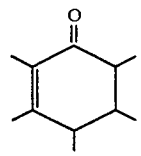

$R^1$ is hydrogen atom, each of $R^2$ and $R^3$ is methoxy group, and Y is methylene group.

According to the present invention, a biphenyl derivative of the formula:

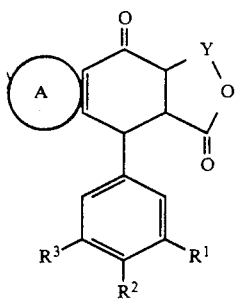
(I-a)

wherein Ring A, $R^1$ to $R^3$ and Y are the same as defined above, can be prepared by the steps of:

[A] reacting a cyanohydrin derivative of the formula:

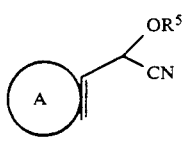
(II)

wherein $R^5O$ is a protected hydroxy group, and Ring A is the same as defined above, with a heterocyclic compound of the formula:

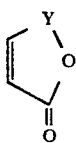

wherein Y is the same as defined above, and an aldehyde compound of the formula:

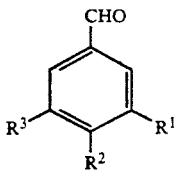

wherein $R^1$ to $R^3$ are the same as defined above,

[B] cyclizing the product in the presence of an acid to give a tetrahydrobiphenyl compound of the formula:

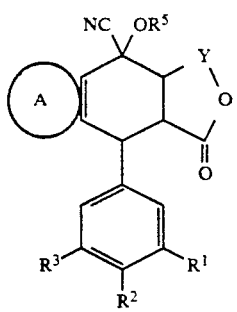

wherein Ring A, $R^1$ to $R^3$, $R^5O$ and Y are the same as defined above, and

[C] treating the compound (V) with a fluorine ion-donor.

On the other hand, a biphenyl derivative of the formula:

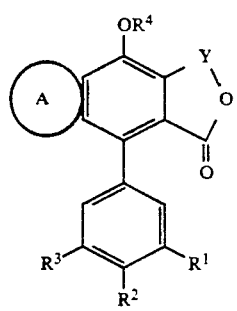

wherein Ring A, $R^1$ to $R^4$ and Y are the same as defined above, can be prepared by the steps of:

[D]
(1) subjecting a dicarboxylate compound of the formula:

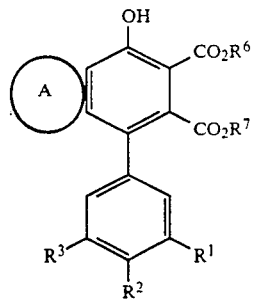

wherein each of $R^6$ and $R^7$ is a lower alkyl group, and Ring A and $R^1$ to $R^3$ are the same as defined above, to reductive lactonization or (2) hydrolyzing the dicarboxylate compound (VI), followed by dehydration thereof, and

[E] condensing the resultant hydroxy-biphenyl compound of the formula:

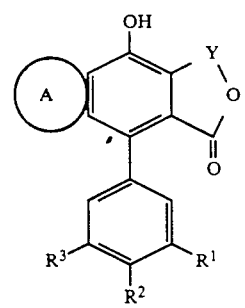

wherein Ring A, $R^1$ to $R^3$ and Y are the same as defined above, with a compound of the formula:

$$R^4-X \quad (VIII)$$

wherein X is a leaving group, and $R^4$ is the same as defined above.

The compound (I-b) may also be prepared by the steps of:

[F] condensing the dicarboxylate compound (VI) with the compound (VIII) to give a dicarboxylate compound of the formula:

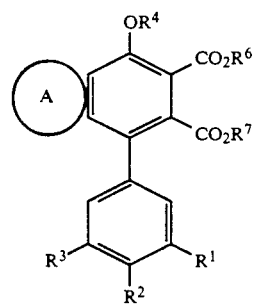

wherein Ring A, $R^1$ to $R^4$, $R^6$ and $R^7$ are the same as defined above, and

[G]
(1) subjecting the compound (IX) to reductive lactonization or (2) hydrolyzing the compound (IX), followed by dehydration thereof.

Alternatively, the compound (I-b) may be prepared by
[H] oxidizing the compound (I-a) to give the hydroxybiphenyl compound (VII) and
[I] condensing it with the compound (VIII).

Further, among the compound (I), a biphenyl derivative of the formula:

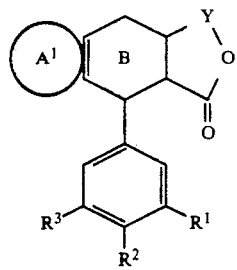

(I-c)

wherein Ring $A^1$ is a sulfur-containing or oxygen-containing heteromonocyclic ring substituted with hydroxymethyl group or a lower alkoxymethyl group, and Ring B, $R^1$ to $R^3$ and Y are the same as defined above, can also be prepared by the step or steps of:
[J] reducing a biphenyl derivative of the formula:

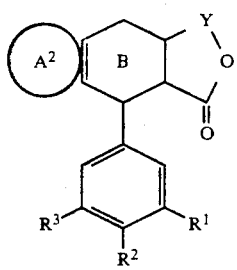

(I-d)

wherein Ring $A^2$ is a sulfur-containing or oxygen-containing heteromonocyclic ring substituted with formyl group, and Ring B, $R^1$ to $R^3$ and Y are the same as defined above, and
[K] if required, alkylating the product.

The reaction of the starting compounds (II), (III) and (IV) (i.e., Step [A]) can be carried out in the presence of a base. Any conventional base may be used for this purpose. Preferred base includes, for example, a lithium dialkylamide, phenyl lithium, a lower alkyl lithium and the like. The protecting group ($R^5$) for the hydroxy group includes any conventional protecting group such as a tri(lower alkyl)silyl group, a diphenyl(lower alkyl)silyl group, a lower alkoxy-lower alkyl group, a lower alkoxy-lower alkoxy-lower alkyl group, a phenyl-lower alkyl group and so forth. The reaction is preferably carried out in a solvent such as tetrahydrofuran, diethyl ether, diglyme, hexane, toluene, xylene or the like and under cooling, for example, at a temperature between −80° and −40° C. Said reaction may be carried out by addition of a base to the mixture of the starting compounds (II), (III) and (IV), but it is usually preferred to carry it out by first condensing the cyanohydrin derivative (II) with the heterocyclic compound (III), and then condensing the product with the aldehyde compound (IV).

The subsequent acid treatment (i.e., Step [B]) can be conducted in a conventional manner. Examples of the acid include organic acids such as acetic acid, trifluoroacetic acid, methanesulfonic acid or p-toluenesulfonic acid; inorganic acids such as sulfuric acid, and the like. Said acid treatment is preferably carried out in the same solvent as employed in the above-mentioned reaction and at ambient temperature or with heating, for example, at a temperature of 10° to 50° C.

The subsequent treatment of the tetrahydrobiphenyl compound (V) with a fluorine ion-donor (i.e., Step [C]) can be conducted in a conventional manner. Any conventional fluorine ion-donor which can releases fluorine ion in the reaction system can be used for the purpose of the invention. Preferred examples of such fluorine ion-donor include hydrogen fluoride, a mixture of a fluoride (e.g., an alkali metal fluoride, ammonium fluoride, a tetra(lower alkyl)ammonium fluoride or the like) and an organic acid and the like. Said treatment is preferably carried out in a solvent such as methylene chloride, chloroform or the like under cooling or at ambient temperature, for example, at a temperature between −20° to 30° C.

On the other hand, the reductive lactonization of dicarboxylate compounds (VI) and (IX) (i.e., Step [D]-(1) and [G]-(1)) can be carried out by treating said compound with a reducing agent, and then, if required, treating the product with an acid. The reducing agents include, for example, a borane-complex, an alkali metal borohydride-boron trifluoride complex, an alkali metal borohydride, an alkaline earth metal borohydride, lithium aluminum hydride and the like. The same organic or inorganic acids as mentioned in Step [B] are preferably used in the reaction. These reactions are preferably carried out in a solvent such as a lower alkanol, tetrahydrofuran, ethyl acetate, dioxane or the like and at ambient temperature or with heating, for example, at a temperature between 10° and 100° C. Concomitantly, when the compound (VI) or (IX) has formyl group on Ring A thereof, such formyl group is simultaneously converted to hydroxy-methyl group during the above-mentioned reductive lactonization.

The hydrolysis and subsequent dehydration of the compounds (VI) and (IX) (i.e., Step [D]-(2) and [G]-(2)) can be conducted in a conventional manner. The hydrolysis is preferably carried out by using a conventional organic or inorganic base such as a tri(lower alkyl)amine, an alkali metal alkoxide, an alkali metal hydroxide or the like. The following dehydration is preferably carried out in the presence of a conventional dehydrating agent such as acetic anhydride, dicyclohexylcarbodiimide, a mixture of p-toluenesulfonyl chloride and pyridine or the like. These reactions are preferably carried out in the same solvent as used in the above-mentioned reductive lactonization and at ambient temperature or with heating, for example, at a temperature between 10° and 100° C. However, when an excess amount of acetic anhydride is used as the dehydrating agent, said dehydration may be carried out without solvent.

The condensation reaction of the compound (VI) or (VII) with the compound (VIII) (i.e., Step [E] and [F]) can be carried out in the presence or absence of an acid acceptor. Examples of the leaving group [X] of the compound (VIII) include a halogen atom, diazo group and the like. Organic bases such as a tri(lower alkyl)amine, pyridine, an N-(lower alkyl)pyperidine and the like and inorganic bases such as an alkali metal carbonate, an alkali metal hydroxide, an alkali metal hydride and the like are preferably used as the acid acceptor. It is preferred to carry out the reactions in a solvent such as N,N-dimethylformamide, tetrahydrofuran, methylene chloride, diethyl ether, dioxane or the like. These reactions preferably proceed at ambient temperature or with ice-cooling or heating, for example, at a temperature between 0° and 100° C. Concomitantly, when the compound (VI) or (VII) has hydroxymethyl group on Ring A thereof, said hydroxy group may, if required, be protected by a lower alkyl group during the reaction.

The oxidation of the compound (I-a) (i.e., Step [H]) can be conducted in a conventional manner. For example, it can be carried out by reacting the compound (I-a) with a halogenating agent, and then treating the product with an organic base such as a tri(lower alkyl)amine or the like or an inorganic base such as an alkali metal hydroxide, an alkali metal bicarbonate or the like. Any conventional halogenating agent may be used for this purpose, but it is usually preferred to use a transition metal halide (e.g., cupric halide) in the presence of an alkali metal halide or the like). Alternatively, said oxidation may be conducted by treating the product with an oxidizing agent such as selenium dioxide, 2,3-dichloro-5,6-dicyanobenzoquinone and the like. It is preferred to carry out the reactions in a solvent (e.g., acetonitrile, chloroform and so forth). These reactions preferably proceed at ambient temperature or with heating, for example, at a temperature between 20° and 85° C.

The condensation reaction of the thus-obtained hydroxybiphenyl compound (VII) with the compound (VIII) (i.e., Step [I]) can be carried out under the same conditions as in step [E].

The reduction of the compound (I-d) (i.e., Step [J]) can be conducted in a conventional manner, for example, by treating it with a reducing agent. Any conventional reducing agents may be used for the reaction, but it is preferred to use a borane complex, an alkali metal borohydride and the like. The reaction is preferably carried out in a solvent (e.g., a lower alkanol, tetrahydrofuran, diglyme, dioxane and so forth). It is preferred to conduct the reaction under cooling or with warming, for example, at a temperature between 0° and 50° C.

The alkylation of the thus-obtained compound having hydroxymethyl group on Ring A thereof (i.e., Step [K]) can be carried out by condensing it with a compound (VIII) under the same conditions as in Steps [E] and [F].

Concomitantly, the above-mentioned methods of the present invention may also be applied, if required, with some appropriate modifications. For example, when Ring A of the compound (V) is an unsubstituted sulfur-containing or oxygen-containing heteromonocyclic group, formyl group may be introduced to said compound (V) by, for example, reacting it with dimethylformamide in the presence of a halogenating agent (e.g., phosphorous oxychloride, thionyl chloride or the like).

In the above-mentioned reactions, the starting compounds of the invention may be used either in a free form or in the form of a salt. For example, the compounds (VI) and (VII), and the compounds (II), (V) and (IX) in which Ring A is substituted with a group having hydroxy group are, if required, used in the form of an alkali metal salt, an alkaline earth metal salt, ammonium salt and the like.

The compound (I) of the present invention has excellent pharmacological activities for alleviating or curing various hepatic injuries such as degeneration or necrosis of hepatocytes, fibrosis, accumulation of fat in liver, congestion of liver and the like. The compound (I) also has excellent liver-protecting activities.

Accordingly, the compound (I) of the present invention is useful as a therapeutic or prophylactic agent for hepatic diseases such as acute or chronic hepatitis, fatty liver, hepatic congestion, hepatocirrhosis and the like in warm-blood animals including human beings. In particular, the compound (I) of the present invention is characterized in that it shows excellent activities in treating or preventing chronic hepatitis or hepatocirrhosis. For example, the compound (I) when administered orally shows excellent curing and/or protecting effects against chronic active hepatitis which are induced 3-hydroxy-4-pyrone [Experientia, Vol. 40, P. 894–896 (1984)]. The compound (I) also suppresses the progress of $CCl_4$-induced fibrosis in the liver [Pharmacological Reviews, Vol. 19, P. 145–208 (1967)], and further shows an excellent therapeutic effect against hepatocirrhosis.

Moreover, the compound (I) of the present invention is low in toxicity and have high safety as a medicine. The compound (I) is also advantageous in that it can be administered repeatedly for a long period because it causes no substantial hepatic hypertrophy usually observed in the known drugs such as Malotilate.

The biphenyl derivatives (I) can be used for pharmaceutical use either in a free form or in the form of a pharmaceutically acceptable salt. Examples of the pharmaceutically acceptable salts include salts with an organic or inorganic base such as alkali metal salts (e.g., potassium salt, sodium salt), alkaline earth metal salts (e.g., calcium salt), ammonium salt, and the like.

Moreover, the biphenyl derivative (I-a) of the present invention may exist in the form of eight optical isomer due to the three asymmetric carbon atoms contained in Ring B. The present invention includes within its scope either one of these optical isomers and a mixture thereof. If required, diastereoisomers may be converted to each other according to a conventional manner. For example, an isomer of the invention having the (r-5, t-6, c-7)-configuration may be converted to the corresponding (r-5, c-6, t-7)-isomer by treating the former with a base (e.g., triethylamine or the like).

The compound (I) and a pharmaceutically acceptable salt thereof may be administered either orally or parenterally, but it is preferred to administer them orally. They may also be used in the form of pharmaceutical preparations such as tablets, capsules, powders, granules, injections and the like, if necessary, in admixture with a pharmaceutically acceptable carrier, diluent or disintegrant.

The dose of the compound (I) or a pharmaceutically acceptable salt thereof may vary depending on the age, body weight and condition of patients, the kind and severity of diseases to be treated, administration route, etc., but it may usually be in the range of about 0.1 to about 500 mg/kg, preferably about 1 to about 300 mg/kg, per day.

Among the starting compounds of the present invention, the cyanohydrin derivative (II) and the dicarboxylate compound (VI) are novel. The compound (II) may be prepared, for example, by reacting an aldehyde compound of the formula:

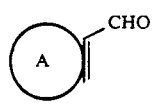

wherein Ring A is the same as defined above, with an alkali metal cyanide and a compound of the formula:

$$R^5\text{—}X^1$$

wherein $X^1$ is a halogen atom and $R^5$ is the same as defined above, in the presence of Lewis acid [e.g., zinc (II) iodide].

On the other hand, the compound (VI) may be prepared, for example, by the steps of:

(1) reacting an acetal compound of the formula:

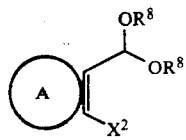

wherein $R^8$ is a lower alkyl group, $X^2$ is hydrogen atom or bromine atom and Ring A is the same as defined above, with an aldehyde compound (IV) in the presence of an alkyl lithium, (2) if required, hydrolyzing the product and/or alkylating or acylating the hydroxy group thereof to give a compound of the formula:

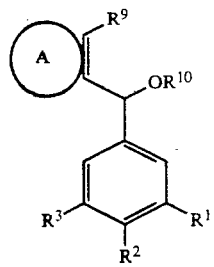

wherein $R^9$ is formyl group or a di(lower alkyl)-methyl group, $R^{10}$ is hydrogen atom, a lower alkyl group or a lower alkanoyl group, and Ring A and $R^1$ to $R^3$ are the same as defined above, and then (3) reacting the thus-obtained product with a di(lower alkyl)acetylenedicarboxylate in the presence of an acid (e.g., trifluoroacetic acid, p-toluenesulfonic acid or the like).

Further, when Ring A of the product has no substituent, formyl group may be introduced to said Ring A in a conventional manner.

In this Specification and Claims, relative configuration of each compound is indicated according to IUPAC Nomenclature of Organic Compound (E-2.3.3 and E-2.3.4). And the terms "a lower alkyl group", "a lower alkoxy group" and "a lower alkanoyl group" represent an alkyl group of one to 4 carbon atoms, an alkoxy group of one to 4 carbon atoms and an alkanoyl group of 2 to 5 carbon atoms, respectively.

EXPERIMENT

Protecting effect against carbon tetrachloride ($CCl_4$)-induced acute liver injury Groups of 3 ddY male mice (weight: 28–35 g) were used. Test compounds suspended in 0.5% sodium carboxymethyl-cellulose (CMC-Na) solution were orally given for 4 consecutive days at a dose of 100 mg/kg/day, and $CCl_4$ was given at a dose of 50 μl/kg [1% (v/v)-olive oil mixture] orally 3 hours after the last administration of test compounds. After a 24 hour fast following the administration of $CCl_4$, the blood was collected into tubes treated with heparin according to the method described in Journal of Pharmacobio-Dynamics, Vol. 10, P. 599–607(1987). After plasma was separated from the blood of mice, glutamic-pyruvic transaminase (GPT) activity was measured. The protective effect (%) against $CCl_4$-induced liver injury was estimated according to the following equation.

$$\text{Protective Effect (\%)} = \left[\frac{GPT(CCl_4) - GPT(T)}{GPT(CCl_4) - GPT(C)}\right] \times 100$$

GPT(T): the average of GPT activity in the medicated group of mice.

GPT($CCl_4$): the average of GPT activity in a group of mice to which a 0.5% CMC-Na solution was administered instead of the test compound solution.

GPT(C): the average of GPT activity in a group of mice to which a 0.5% CMC-Na solution and olive oil were administered instead of the test compound solution and the $CCl_4$ solution, respectively.

LIST OF COMPOUNDS TESTED

No. 1: 2, r-5-bis(hydroxymethyl)-4-oxo-t-7-(3,4-dimethoxyphenyl)-4,5,6,7-tetrahydrobenzo[b]furan-c-6-carboxylic acid γ-lactone No. 2: 4-oxo-r-5-hydroxymethyl-t-7-(3,4-dimethoxyphenyl)-4,5,6,7-tetrahydrobenzo[b]furan-c-6-carboxylic acid lactone No. 3: 4-methoxy-7-(3,4-dimethoxyphenyl)benzo[b]thiophen-5,6-dicarboxylic acid anhydride No. 4: 4-methoxy-5-hydroxymethyl-7-(3,4-dimethoxyphenyl)benzo[b]thiophen-6-carboxylic acid lactone No. 5: 4-methoxy-5-hydroxymethyl-7-(3,4-dimethoxyphenyl)benzo[b]furan-6-carboxylic acid lactone No. 6: 4-methoxy-5-hydroxymethyl-7-(4-methoxyphenyl)benzo[b]thiophen-6-carboxylic acid lactone No. 7: 4-methoxymethoxy-5-hydroxymethyl-7-(3,4-dimethoxyphenyl)benzo[b]thiophen-6-carboxylic acid lactone No. 8: 4-ethoxycarbonylmethoxy-5-hydroxymethyl-7-(3,4-dimethoxyphenyl)benzo[b]thiophen-6-carboxylic acid lactone No. 9: 4-methoxy-5-hydroxymethyl-7-(3,4-dichlorophenyl)benzo[b]thiophen-6-carboxylic acid lactone No. 10: 4-methoxy-5-hydroxymethyl-7-(3,4,5-trimethoxyphenyl)benzo[b]thiophen-6-carboxylic acid lactone No. 11: 2-methoxymethyl-4-methoxy-5-hydroxymethyl-7-(3,4-dimethoxyphenyl)benzo[b]thiophen-6-carboxylic acid lactone The results are shown in the following Table 1.

TABLE 1

| Test Comp. Nos. | Protective Effect (%) |
|---|---|
| 1 | 56.8 |
| 2 | 79.4 |
| 3 | 63.7 |
| 4 | 55.2 |
| 5 | 28.3 |
| 6 | 28.5 |
| 7 | 24.3 |
| 8 | 28.3 |
| 9 | 22.7 |
| 10 | 31.7 |
| 11 | 22.9 |

EXAMPLE 1

(1) 188 g of potassium cyanide, 384 g of tert.-butyldimethylsilyl chloride, 185 g of 3-furylaldehyde and 18 g of zinc iodide are added to 1.5 liters of acetonitrile and the mixture is stirred at ambient temperature for 2 days. 3 liters of diethyl ether are added to the reaction mixture, and the insoluble materials are filtered off. The filtrate is condensed, and the residue is dissolved in diethyl ether. The mixture is washed with water, dried and condensed. The residue is further distilled under reduced pressure to give 416 g of 2-(3-furyl)-2-(tert.-butyldimethylsilyloxy)acetonitrile.

B.p. 90° to 100° C./1 to 2 mmHg.

NMR(CDCl$_3$, $\delta$): 0.16 (s, 3H), 0.21 (s, 3H), 0.93 (s, 9H), 5.47 (s, 1H), 6.4–6.6 (m, 1H), 7.3–7.5 (m, 1H), 7.5–7.6 (m, 1H).

(2) A solution of 267 g of the product obtained in paragraph (1) in 300 ml of toluene, a solution of 97.4 g of 2-oxo-2,5-dihydrofuran in 1.5 liters of toluene and a solution of 192 g of 3,4-dimethoxybenzaldehyde in 300 ml of toluene are added dropwise in this order to a lithium diisopropylamide solution [prepared from 129 g of diisopropylamine and 1.28 mole of n-butyl lithium in hexane-toluene at −78° C.]. 146 ml of acetic acid and one liter of water are further added to the reaction mixture. The organic layer is separated, washed with water, dried and evaporated under reduced pressure to remove the solvent. 560 g of crude 2-oxo-3-($\alpha$-hydroxy-3,4-dimethoxy-benzyl)-4-[(3-furyl)(tert.-butyldimethylsilyloxy)cyanomethyl]-2,3,4,5-tetrahydrofuran are obtained.

(3-a) 560 g of the crude product obtained in paragraph (2) are dissolved in one liter of methylene chloride, and 500 ml of trifluoroacetic acid are added thereto. The mixture is allowed to stand at ambient temperature overnight. The reaction mixture is diluted with one liter of chloroform, washed with water, dried and evaporated to remove the solvent. The residue is recrystallized from diethyl ether to give 304 g of 4-(tert.-butyldimethylsilyloxy)-4-cyano-5-hydroxymethyl-7-(3,4-dimethoxyphenyl)-4,5,6,7-tetrahydrobenzo[b]furan-6-carboxylic acid lactone. This product is a mixture of (r-4, c-5, t-6, c-7)-isomer and (r-4, t-5, c-6, t-7)-isomer.

M.p. 152° to 156° C.

(3-b) 560 g of the crude product obtained in paragraph (2) are dissolved in 1.4 liters of dioxane, and 270 ml of methanesulfonic acid are added thereto. The mixture is stirred at ambient temperature for 3 hours. 4 liters of chloroform are added thereto, and the mixture is washed with water, dried and evaporated to remove the solvent. The residue is triturated with methanol, and crystalline precipitates are collected by filtration, washed with methanol and dried. 267 g of 4-(tert.-butyldimethylsilyloxy)-4-cyano-5-hydroxymethyl-7-(3,4-dimethoxyphenyl)-4,5,6,7-tetrahydrobenzo[b]furan-6-carboxylic acid lactone are obtained as a mixture of (r-4, c-5, t-6, c-7)-isomer and (r-4, t-5, c-6, t-7)-isomer.

The physico-chemical properties of this product are identical with those of the product obtained in paragraph (3-a).

(4) 32.6 g of phosphorus oxychloride are added dropwise to 100 ml of N,N-dimethylformamide under ice-cooling, and the mixture is stirred at ambient temperature for 30 minutes. A solution of 20 g of the product obtained in paragraph (3-a) or (3-b) in 100 ml of N,N-dimethylformamide are added thereto, and the mixture is stirred at 50° to 60° C. for 6 hours. The reaction mixture is poured into ice-water and extracted with ethyl acetate. The extract is washed with water, dried and evaporated to remove the solvent. The residue is purified by silica gel column chromatography [solvent: hexane-chloroform (1:10)]. The eluate is evaporated to remove the solvent, and diethyl ether is added to the residue. The crystalline precipitates are collected by filtration. 11.4 g of 2-formyl-4-(tert.-butyldimethylsilyloxy)-4-cyano-5-hydroxymethyl-7-(3,4-dimethoxyphenyl)-4,5,6,7-tetrahydrobenzo[b]furan-6-carboxylic acid lactone are obtained as a mixture of (r-4, c-5, t-6, c-7)-isomer and (r-4, t-5, c-6, t-7)-isomer.

M.p. 150° to 154° C.

(5) 6.5 g of the product obtained in paragraph (4) are dissolved in 50 ml of methylene chloride, and 1.18 g of acetic acid and 15.7 ml of a 1M solution of tetra(n-butyl)ammonium fluoride in tetrahydrofuran are added thereto under ice-cooling. Five minutes later, the reaction mixture is washed with water, dried and evaporated to remove the solvent. The residue is added to 100 ml of toluene, and the mixture is refluxed with heating for 3 hours. The reaction mixture is evaporated to remove the solvent, and the residue is purified by silica gel column chromatography [solvent: hexane-ethyl acetate (1:1)]. The eluate is condensed, and the residue is recrystallized from a mixture of ethyl acetate and hexane. 3.5 g of 2-formyl-4-oxo-r-5-hydroxymethyl-t-7-(3,4-dimethoxyphenyl)-4,5,6,7-tetrahydrobenzo[b]furan-c-6-carboxylic acid lactone are obtained.

M.p. 182° to 184° C.

EXAMPLE 2

1.0 g of 2-formyl-4-oxo-r-5-hydroxymethyl-t-7-(3,4-dimethoxyphenyl)-4,5,6,7-tetrahydrobenzo[b]furan-c-6-carboxylic acid lactone is dissolved in 100 ml of isopropyl alcohol, and 2.0 g of sodium borohydride are added gradually thereto. Then, the mixture is stirred at ambient temperature for 2 hours. Acetic acid is added thereto, and insoluble materials are filtered off. The filtrate is evaporated to remove the solvent, and the residue is dissolved in chloroform. The mixture is washed with water, dried and evaporated to remove the solvent, and the residue is recrystallized from ethyl acetate. 670 mg of 2, r-5-bis(hydroxymethyl)-4-oxo-t-7-(3,4-dimethoxyphenyl)-4,5,6,7-tetrahydrobenzo[b]furan-c-6-carboxylic acid $\gamma$-lactone are obtained.

M.p. 154° to 156° C.

EXAMPLE 3

2.06 g of 4-(tert.-butyldimethylsilyloxy)-4-cyano-5-hydroxymethyl-7-(3,4-dimethoxyphenyl)-4,5,6,7-tetrahydrobenzo[b]furan-6-carboxylic acid lactone [a mixture of (r-4, c-5, t-6, c-7)-isomer and (r-4, t-5, c-6, t-7)-isomer] and 0.35 ml of acetic acid are dissolved in 20 ml of methylene chloride. 5.3 ml of a 1M solution of tetra(n-butyl)ammonium fluoride in tetrahydrofuran are added dropwise thereto under ice-cooling, and the mixture is stirred at ambient temperature overnight. The reaction mixture is washed with water, dried and evaporated to remove the solvent. The residue is recrystallized from ethyl acetate. 1.23 g of 4-oxo-r-5-hydroxymethyl-t-7-(3,4-dimethoxyphenyl)-4,5,6,7-tetrahydrobenzo[b]furan-c-6-carboxylic acid lactone are obtained.

M.p. 165.9° C.

EXAMPLE 4

(1-a) 23.0 g of 4-(tert.-butyldimethylsilyloxy)-4-cyano-5-hydroxymethyl-7-(3,4-dimethoxyphenyl)-4,5,6,7-tetrahydrobenzo[b]furan-6-carboxylic acid lactone [a mixture of (r-4, c-5, t-6, c-7)-isomer and (r-4, t-5, c-6, t-7)-isomer] and 6.9 g of ammonium fluoride are added to a mixture of 207 ml of acetonitrile and 23 ml of water. The mixture is stirred at ambient temperature for 20 hours. The reaction mixture is poured into water, and the crystalline precipitates are collected by filtration, washed with water-methanol and dried. 14.3 g of 4-oxo-r-5-hydroxymethyl-c-7-(3,4-dimethoxyphenyl)-4,5,6,7-tetrahydrobenzo[b]furan-t-6-carboxylic acid lactone are obtained.

M.p. 210° to 212° C.

(1-b) 200 g of 4-(tert.-butyldimethylsilyloxy)-4-cyano-5-hydroxymethyl-7-(3,4-dimethoxyphenyl)-4,5,6,7-tetrahydrobenzo[b]furan-6-carboxylic acid lactone [a mixture of (r-4, c-5, t-6, c-7)-isomer and (r-4, t-5, c-6, t-7)-isomer] and 30.8 g of acetic acid are dissolved in 500 ml of methylene chloride. 448 ml of a 1M tetrahydrofuran solution of tetra(n-butyl)ammonium fluoride are added dropwise thereto at −20° to −10° C., and the mixture is stirred at −10° C. for 10 minutes. The reaction mixture is poured into diethyl ether, and insoluble materials are filtered off. 92 g of 4-oxo-r-5-hydroxymethyl-c-7-(3,4-dimethoxyphenyl)-4,5,6,7-tetrahydrobenzo[b]furan-t-6-carboxylic acid lactone are obtained.

The physico-chemical properties of this product are identical with those of the product obtained in paragraph (1-a).

(2) 14.3 g of the product obtained in paragraph (1-a) or (1-b) are suspended in 200 ml of toluene, and 5 ml of triethylamine are added thereto. The mixture is refluxed with heating for 5.5 hours. 5 ml of triethylamine are added to the mixture, and the mixture is further refluxed with heating for 4.5 hours. The reaction mixture is evaporated to remove the solvent, and the residue is recrystallized from ethyl acetate. 12.48 g of 4-oxo-r-5-hydroxymethyl-t-7-(3,4-dimethoxyphenyl)-4,5,6,7-tetrahydrobenzo[b]furan-c-6-carboxylic acid lactone are obtained.

The physico-chemical properties of this product are identical with those of the product obtained in Example 3.

EXAMPLES 5 AND 6

The corresponding starting materials are treated in the same manner as described in either one of Examples 1 to 4 to give the compounds in the following Table 2.

TABLE 2

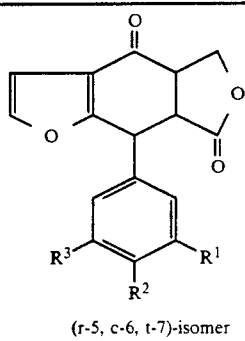

(r-5, c-6, t-7)-isomer

TABLE 2-continued

| Ex. Nos. | $R^1$, $R^2$, $R^3$ substituents | Melting points |
|---|---|---|
| 5 | 3,4-methylenedioxyphenyl | 156 to 158° C. |
| 6 | phenyl | 116 to 119° C. |

EXAMPLE 7

(1) 224 g of 3-thiophenecarbaldehyde and 265 g of methyl orthoformate are dissolved in 200 ml of methanol. One g of strongly acidic ion-exchange resin Amberlite IR-120(H+) [manufactured by Rohm & Haas] is added thereto, and the mixture is refluxed with heating for 2 hours. The resin is separated by filtration, and the filtrate is condensed under reduced pressure. The residue is distilled to give 294 g of 3-dimethoxymethylthiophene.

B.p. 65° C./4 mmHg.

(2) 10.0 g of the product obtained in paragraph (1) are dissolved in 100 ml of tetrahydrofuran. 45 ml of a 1.55M n-butyl lithium solution in hexane are added thereto under stirring at −70° to −50° C. for about 10 minutes. After the mixture is stirred at −70° to −60° C. for 30 minutes, a solution of 10.5 g of 3,4-dimethoxybenzaldehyde in 50 ml of tetrahydrofuran are added thereto. Said addition is carried out at a temperature of −70° to −50° C. for about 10 minutes. The mixture is stirred at the same temperature for 30 minutes, and then, poured into 300 ml of water. 500 ml of ethyl acetate are added thereto, and an organic layer is separated after shaking. Said organic layer is dried and evaporated under reduced pressure to remove the solvent. The residue is purified by silica gel column chromatography [solvent: hexane-ethyl acetate (2:1)]. The eluate is evaporated to remove the solvent. 18.0 g of 3-dimethoxymethyl-2-(α-hydroxy-3,4-dimethoxybenzyl)thiophene are obtained as an oil.

(3-a) 1.9 g of boric acid are added to a solution of one g of the product obtained in paragraph (2) in 20 ml of toluene, and the mixture is refluxed with heating. After cooled, the mixture is evaporated to remove the solvent, and 50 ml of ethyl acetate are added to the residue. The mixture is washed with water, dried and evaporated under reduced pressure to remove the solvent. The residue is purified by silica gel column chromatography [solvent: hexane-ethyl acetate (1:1)], and the eluate is evaporated to remove the solvent. 470 mg of 2-(α-hydroxy-3,4-dimethoxybenzyl)thiophen-3-carbaldehyde are obtained as colorless crystals.

M.p. 90° to 91° C.

(3-b) 6.0 g of sodium hydride are suspended in 300 ml of tetrahydrofuran. A tetrahydrofuran solution containing 81.0 g of the product obtained in paragraph (2) and 18.8 ml of methyl iodide are added thereto successively. The mixture is stirred overnight. Water is added thereto and the mixture is extracted with chloroform. The extract is dried and evaporated under reduced pressure to remove the solvent. The residue is purified by silica gel column chromatography [solvent: hexane-ethyl acetate (1:1)], and the eluate is condensed. 67.7 g of 3-dimethoxymethyl-2-(α-methoxy-3,4-dimethoxybenzyl)thiophene are obtained as an oil.

NMR(CDCl$_3$, δ): 3.23 (s, 3H), 3.30 (s, 3H), 3.47 (s, 3H), 3.84 (s, 6H), 5.44 (s, 1H), 5.68 (s, 1H), 6.73–7.38 (m, 5H).

(4) 160 g of the product obtained in paragraph (3-a) are dissolved in 500 ml of methylene chloride. 60 ml of acetic anhydride and 0.5 g of 4-dimethylaminopyridine are added thereto. The mixture is cooled below 10° C. 97 ml of triethylamine are added dropwise thereto at the same temperature, and the mixture is stirred at ambient temperature for one hour. Water is added to the reaction mixture. The organic layer is separated, and the aqueous layer is further extracted with methylene chloride. Both of the organic layers are combined, washed with aqueous sodium bicarbonate solution and water, dried and evaporated under reduced pressure to remove the solvent. The residue is recrystallized from toluene to give 162 g of 2-(α-acetoxy-3,4-dimethoxybenzyl)thiophen-3-carbaldehyde.

M.p. 91° to 92° C.

(5-a) 10.0 g of the product obtained in paragraph (2) and 4.3 g of dimethyl acetylenedicarboxylate are dissolved in 50 ml of toluene with heating. 0.05 ml of trifluoroacetic acid is added thereto, and the mixture is refluxed for 5 hours. The reaction mixture is evaporated under reduced pressure to remove the solvent. The residue is recrystallized from toluene to give 7.1 g of 4-hydroxy-5,6-bis(methoxycarbonyl)-7-(3,4-dimethoxyphenyl)benzo[b]thiophene as colorless prisms.

M.p. 147° to 148° C.

(5-b) 68.4 g of the product obtained in paragraph (3-a), 35 g of dimethyl acetylenedicarboxylate and 0.5 ml of trifluoroacetic acid are dissolved in 350 ml of toluene. The mixture is refluxed for 2 hours and evaporated under reduced pressure to remove the solvent. The residue is recrystallized from toluene to give 78.2 g of 4-hydroxy-5,6-bis(methoxycarbonyl)-7-(3,4-dimethoxyphenyl)benzo[b]thiophene as colorless prisms.

The physico-chemical properties of this product are identical with those of the product obtained in paragraph (5-a).

(5-c) 60 g of the product obtained in paragraph (4), 34.4 g of dimethyl acetylenedicarboxylate and 0.6 ml of trifluoroacetic acid are dissolved in 300 ml of benzene. The mixture is refluxed with heating for 10 hours. 0.3 ml of trifluoroacetic acid is added thereto, and the mixture is further refluxed for 5 hours. The reaction mixture is evaporated under reduced pressure to remove the solvent, and the residue is recrystallized from toluene. 60.3 g of 4-hydroxy-5,6-bis(methoxycarbonyl)-7-(3,4-dimethoxyphenyl)benzo[b]thiophene are obtained as colorless prisms.

The physico-chemical properties of this product are identical with those of the product obtained in paragraph (5-a).

(5-d) The product obtained in paragraph (3-b) is treated in the same manner as described in either one of (5-a), (5-b) of (5-c). 4-hydroxy-5,6-bis(methoxycarbonyl)-7-(3,4-dimethoxyphenyl)benzo[b]thiophene are obtained as colorless prisms.

The physico-chemical properties of this product are identical with those of the product obtained in paragraph (5-a).

(6) 35.0 g of the product obtained in either one of paragraph (5-a), (5-b), (5-c) or (5-d) are dissolved in 20 ml of N,N-dimethylformamide. The solution is added dropwise to a suspension of 4.17 g of sodium hydride in 100 ml of N,N-dimethylformamide. The mixture is stirred at ambient temperature for one hour. 14.8 g of methyl iodide are added thereto. The mixture is stirred at ambient temperature for 3 hours and evaporated under reduced pressure to remove the solvent. The residue is recrystallized from ethyl acetate to give 22.6 g of 4-methoxy-5,6-bis(methoxycarbonyl)-7-(3,4-dimethoxyphenyl)benzo[b]thiophene.

M.p. 118° C.

(7) 4.0 g of sodium hydroxide are dissolved in a mixture of 30 ml of ethanol and 30 ml of water. 4.0 g of the product obtained in paragraph (6) are added thereto, and the mixture is refluxed with heating for 5 hours. After cooled down to ambient temperature, the mixture is acidified with diluted hydrochloric acid and extracted with ethyl acetate. The extract is dried and evaporated to remove the solvent. The residue is dried under reduced pressure and dissolved in 15 ml of acetic anhydride. The solution is refluxed with heating for one hour and evaporated under reduced pressure to remove the solvent. The residue is recrystallized from ethyl acetate to give 2.6 g of 4-methoxy-7-(3,4-dimethoxyphenyl)benzo[b]thiophen-5,6-dicarboxylic anhydride M.p. 201° to 202° C.

EXAMPLE 8

4-hydroxy-5,6-bis(methoxycarbonyl)-7-(3,4-dimethoxyphenyl)benzo[b]thiophene is treated in the same manner as described in Example 7-(7). The thus-obtained product is treated in the same manner as described in Example 7-(6) to give 4-methoxy-7-(3,4-dimethoxyphenyl)benzo[b]thiophen-5,6-dicarboxylic anhydride.

The physico-chemical properties of this product are identical with those of the product obtained in Example 7-(7).

EXAMPLE 9

(1) 75.5 g of 4-hydroxy-5,6-bis(methoxycarbonyl)-7-(3,4-dimethoxyphenyl)benzo[b]thiophene are dissolved in 250 ml of tetrahydrofuran. 21.6 ml of 10M borane-dimethylsulfide complex are added dropwise thereto at a temperature below 10° C. The mixture is stirred at 10° C. for one hour. After slowly warmed up to ambient temperature, the mixture is stirred at the same temperature overnight and evaporated under reduced pressure to remove the solvent. 170 ml of methanol and 2 ml of trifluoroacetic acid are added to the residue, and the mixture is refluxed with heating for 12 hours. After the reaction mixture is cooled down to ambient temperature, crystalline precipitates are collected by filtration, washed with methanol and dried with air. 66.6 g of 4-hydroxy-5-hydroxymethyl-7-(3,4-dimethoxyphenyl)-benzo[b]thiophen-6-carboxylic acid γ-lactone are obtained as pale yellow crystals.

M.p. 221° to 222° C.

(2) 22.2 g of the product obtained in paragraph (1) are added to a suspension of 1.86 g of sodium hydride in 350 ml of tetrahydrofuran. The mixture is stirred at ambient temperature for 30 minutes. 4.83 g of methyl iodide and 20 ml of N,N-dimethylformamide are added thereto. The mixture is stirred overnight. The reaction mixture is evaporated under reduced pressure to remove the solvent. The residue is recrystallized from toluene to give 18.8 g of 4-methoxy-5-hydroxymethyl-7-(3,4-dimethoxyphenyl)benzo[b]thiophen-6-carboxylic acid γ-lactone.

M.p. 186° C.

EXAMPLE 10

4-methoxy-5,6-bis(methoxycarbonyl)-7-(3,4-dimethoxyphenyl)benzo[b]thiophene is treated in the same manner as described in Example 9-(1) to give 4-methoxy-5-hydroxymethyl-7-(3,4-dimethoxyphenyl)-benzo[b]thiophen-6-carboxylic acid lactone.

The physico-chemical properties of this product are identical with those of the product obtained in Example 9-(2).

EXAMPLE 11

(1) 20 g of 4-oxo-r-5-hydroxymethyl-t-7-(3,4-dimethoxyphenyl)-4,5,6,7-tetrahydrobenzo[b]furan-c-6-carboxylic acid lactone, 54.4 g of cupric bromide and 5.30 g of lithium bromide are dissolved in 300 ml of acetonitrile. The mixture is stirred with heating for 15 hours. The reaction mixture is evaporated under reduced pressure to remove the solvent. Water is added to the residue. The mixture is acidified with hydrochloric acid and extracted with chloroform. The extract is dried and evaporated to remove the solvent. Diethyl ether is added to the residue, and crystalline precipitates are collected by filtration and dried. 11.9 g of 4-hydroxy-5-hydroxymethyl-7-(3,4-dimethoxyphenyl)benzo[b]furan-6-carboxylic acid lactone are obtained.

M.p. 255° C.

(2) A solution of 2.94 g of the product obtained in paragraph (1) in 10 ml of N,N-dimethylformamide are added dropwise to a suspension of 0.32 g of sodium hydride in 30 ml of N,N-dimethylformamide. The mixture is stirred at ambient temperature for 30 minutes. 1.92 g of methyl iodide are added thereto. The mixture is stirred at ambient temperature for 4 hours and evaporated under reduced pressure to remove the solvent. Water is added to the residue, and the mixture is extracted with chloroform. The extract is dried and evaporated under reduced pressure to remove the solvent. The residue is purified by silica gel column chromatography [solvent: hexane-ethyl acetate (1:1)]. The eluate is condensed to give 1.65 g of 4-methoxy-5-hydroxymethyl-7-(3,4-dimethoxyphenyl)benzo[b]furan-6-carboxylic acid lactone.

M.p. 214° C.

EXAMPLES 12 TO 21

The corresponding starting materials are treated in the same manner either as described in Example 7-(1) to (5-d) and Example 9 or 10, or as described in Example 3 or 4 and Example 11 to give the compounds shown in the following Table 3.

TABLE 3

General structure: benzo[b]thiophene with OR⁴ group, lactone, and phenyl substituent bearing R¹, R², R³.

| Ex. Nos. | R⁴ | R¹/R²/R³ phenyl substituent | Melting points |
|---|---|---|---|
| 12 | —CH₃ | phenyl (unsubstituted) | 176° C. |
| 13 | —CH₃ | 4-OCH₃ phenyl | 183° C. |
| 14 | —C₂H₅ | 3-OCH₃, 4-OCH₃ phenyl | 178 to 179° C. |
| 15 | —(CH₂)₃CH₃ | 3-OCH₃, 4-OCH₃ phenyl | 180 to 182° C. |
| 16 | —CH₂OCH₃ | 3-OCH₃, 4-OCH₃ phenyl | 176° C. |
| 17 | —CH₂CO₂C₂H₅ | 3-OCH₃, 4-OCH₃ phenyl | 151 to 152° C. |
| 18 | —CH₃ | 3-OCH₃, 4-OC₂H₅ phenyl | 186 to 187° C. |
| 19 | | 3-OC₂H₅, 4-OC₂H₅ phenyl | 165 to 167° C. |
| 20 | —CH₃ | 3-Cl, 4-Cl phenyl | 210° C. |
| 21 | | 3-OCH₃, 4-OCH₃, 5-OCH₃ phenyl | 170 to 171° C. |

EXAMPLE 22

(1) 16.9 g of 3-dimethoxymethyl-2-(α-methoxy-3,4-dimethoxybenzyl)thiophene are dissolved in 200 ml of tetrahydrofuran. 37.5 ml of 1.6M n-butyl lithium in hexane are added dropwise thereto at −78° C., and the reaction mixture is warmed up to −30° C. gradually. After the mixture is chilled at −78° C., 4.3 ml of N,N-dimethylformamide are added thereto. The mixture is stirred for 30 minutes. The reaction mixture is warmed up to ambient temperature. The mixture is acidified with diluted sulfuric acid, stirred for one hour and extracted with chloroform. The extract is washed with aqueous sodium bicarbonate solution and water, dried and evaporated under reduced pressure to remove the solvent. The residue is purified by silica gel column chromatography [solvent: hexane-ethyl acetate (2:1)], and the eluate is condensed. 14.6 g of 2-(α-methoxy-3,4-dimethoxybenzyl)thiophen-3,5-dicarbaldehyde are obtained as an oil.

NMR(CDCl$_3$, δ): 3.40 (s, 3H), 3.86 (s, 6H), 6.05 (s, 1H), 6.78–7.12 (m, 3H), 8.02 (s, 1H), 9.86 (s, 1H), 9.99 (s, 1H).

(2) 14.6 g of the product obtained in paragraph (1), 7.4 ml of dimethyl acetylenedicarboxylate and one ml of trifluoroacetic acid are dissolved in 150 ml of benzene. The mixture is refluxed with heating for 20 hours and evaporated under reduced pressure to remove the solvent. The residue is purified by silica gel column chromatography [solvent: hexane-ethyl acetate (2:1)], and the eluate is condensed. 8.33 g of 4-hydroxy-5,6-bis(methoxycarbonyl)-7-(3,4-dimethoxyphenyl)benzo[b]thiophen-2-carbaldehyde are obtained as an oil.

NMR(CDCl$_3$, δ): 3.62 (s, 3H), 3.86 (s, 3H), 3.93 (s, 6H), 6.92 (s, 3H), 8.26 (s, 1H), 9.96 (s, 1H).

(3) 8.33 g of the product obtained in paragraph (2) are dissolved in 50 ml of tetrahydrofuran. 4.5 ml of 10M boranedimethylsulfide complex are added thereto under ice-cooling. The mixture is stirred at ambient temperature overnight and evaporated under reduced pressure to remove the solvent. 30 ml of methanol and catalytic amount of trifluoroacetic acid are added to the residue. The mixture is refluxed with heating for 3 hours and cooled down to ambient temperature. Crystalline precipitates are collected by filtration, washed with methanol and dried with air. 5.75 g of 4-hydroxy-2,5-bis(hydroxymethyl)-7-(3,4-dimethoxyphenyl)benzo[b]thiophen-6-carboxylic acid γ-lactone are obtained.

NMR(d$_6$-DMSO, δ): 3.75 (s, 3H), 3.93 (s, 3H), 4.63–4.87 (m, 2H), 5.26–5.38 (m, 2H), 5.50–5.85 (m, 1H), 6.93–7.13 (m, 3H), 7.52 (s, 1H).

(4) 1.25 g of the product obtained in paragraph (3), 0.70 g of potassium carbonate and 0.27 ml of methyl iodide are dissolved in 20 ml of N,N-dimethylformamide. The mixture is stirred at ambient temperature for 4 hours and evaporated under reduced pressure to remove the solvent. Water is added to the residue, and the mixture is extracted with chloroform. The extract is dried and evaporated under reduced pressure to remove the solvent. The residue is purified by silica gel column chromatography [solvent: ethyl acetate], and the eluate is condensed. 0.97 g of 2,5-bis(hydroxymethyl)-4-methoxy-7-(3,4-dimethoxyphenyl)benzo[b]thiophen-6-carboxylic acid γ-lactone is obtained.

M.p. 164° C.

EXAMPLE 23

1.25 g of 4-hydroxy-2,5-bis(hydroxymethyl)-7-(3,4-dimethoxyphenyl)benzo[b]thiophen-6-carboxylic acid γ-lactone are dissolved in 5 ml of N,N-dimethylformamide. Said solution is added dropwise to a suspension of 0.20 g of sodium hydride in 20 ml of N,N-dimethylformamide. The mixture is stirred at ambient temperature for 30 minutes. 1.20 g of methyl iodide are added thereto. The mixture is stirred at ambient temperature for 3 hours and evaporated under reduced pressure to remove the solvent. The water is added to the residue, and the mixture is extracted with chloroform. The extract is dried and evaporated under reduced pressure to remove the solvent. The residue is purified by silica gel column chromatography [solvent: ethyl acetate], and the eluate is condensed. 0.97 g of 2-methoxymethyl-4-methoxy-5-hydroxymethyl-7-(3,4-dimethoxyphenyl)-benzo[b]thiophen-6-carboxylic acid lactone is obtained. M.p. 175° to 176° C.

EXAMPLE 24

2,5-bis(hydroxymethyl)-4-methoxy-7-(3,4-dimethoxyphenyl)benzo[b]thiophen-6-carboxylic acid γ-lactone is treated in the same manner as described in Example 23. 2-methoxymethyl-4-methoxy-5-hydroxymethyl-7-(3,4-dimethoxyphenyl)benzo[b]thiophen-6-carboxylic acid lactone is obtained.

The physico-chemical properties of this product are identical with those of the product obtained in Example 23.

What we claim is:

1. A benzofuran derivative of the formula:

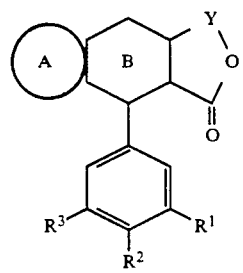

wherein Ring A is a ring of the formula

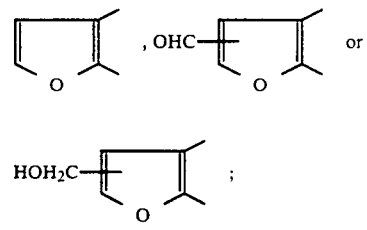

ring B is a ring of the formula

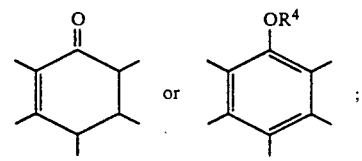

R$^1$ is hydrogen; each of R$^2$ and R$^3$ is hydrogen or lower alkoxy, or R$^2$ and R$^3$ are combined together to form lower alkylenedioxy; R$^4$ is lower alkyl; and Y is methylene, or a pharmaceutically acceptable salt thereof.

2. A compound claimed in claim 1, in which Ring A is a ring of the formula:

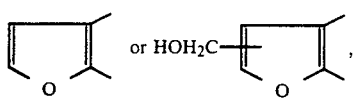

and each of R² and R³ is lower alkoxy.

3. A compound claimed in claim 2 in which Ring B is a ring of the formula:

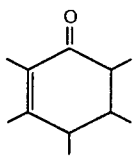

and each of R² and R³ is methoxy.

4. A pharmaceutical composition which comprises a pharmaceutically effective amount of the compound claimed in claim 1 and a pharmaceutically acceptable carrier, diluent or disintegrant.

5. A method for treatment or prophylaxis of hepatic diseases in a warm-blood animal which comprises administering to said warm-blood animal a pharmaceutically effective amount of the compound claimed in claim 1.

* * * * *